(12) United States Patent
Maschke et al.

(10) Patent No.: US 7,740,589 B2
(45) Date of Patent: Jun. 22, 2010

(54) METHOD AND APPARATUS FOR TRAINING ADJUSTMENT IN SPORTS, IN PARTICULAR IN RUNNING SPORTS

(75) Inventors: Michael Maschke, Lonnerstadt (DE); Martin Kleen, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 1219 days.

(21) Appl. No.: 10/895,697

(22) Filed: Jul. 21, 2004

(65) Prior Publication Data

US 2005/0021110 A1 Jan. 27, 2005

(51) Int. Cl.
*A61B 5/02* (2006.01)
(52) U.S. Cl. .................................... 600/500
(58) Field of Classification Search .......... 482/8–9
See application file for complete search history.

(56) References Cited

U.S. PATENT DOCUMENTS

| | | | | |
|---|---|---|---|---|
| 3,412,729 A * | 11/1968 | Smith, Jr. | | 600/324 |
| 4,911,167 A | 3/1990 | Corenman et al. | | |
| 5,076,271 A * | 12/1991 | Lekholm et al. | | 607/22 |
| RE35,122 E | 12/1995 | Corenman et al. | | |
| 5,497,769 A * | 3/1996 | Gratton et al. | | 600/323 |
| 5,746,206 A | 5/1998 | Mannheimer | | |
| 5,800,348 A | 9/1998 | Kaestle | | |
| 5,853,351 A * | 12/1998 | Maruo et al. | | 482/8 |
| 6,411,841 B2 * | 6/2002 | Heikkila | | 600/513 |
| 6,736,759 B1 * | 5/2004 | Stubbs et al. | | 482/8 |
| 6,899,676 B1 | 5/2005 | Stegmann | | |
| 6,920,348 B2 * | 7/2005 | Vasin et al. | | 600/509 |
| 2002/0161290 A1 * | 10/2002 | Chance | | 600/323 |
| 2003/0050541 A1 | 3/2003 | Wuori | | |
| 2004/0147850 A1 * | 7/2004 | Amano et al. | | 600/513 |
| 2004/0260191 A1 * | 12/2004 | Stubbs et al. | | 600/520 |
| 2005/0164832 A1 * | 7/2005 | Maschke | | 482/8 |
| 2007/0179350 A1 * | 8/2007 | Nadeau | | 600/300 |
| 2009/0029769 A1 * | 1/2009 | Muller | | 463/31 |

FOREIGN PATENT DOCUMENTS

| | | |
|---|---|---|
| DE | 696 04 464 T2 | 1/2000 |
| DE | 199 09 852 | 9/2000 |
| DE | 199 09 852 A1 | 9/2000 |
| EP | 0 261 788 | 3/1988 |
| EP | 0 761 159 B1 | 3/1997 |

* cited by examiner

*Primary Examiner*—Patricia C Mallari
*Assistant Examiner*—Karen E Toth
(74) *Attorney, Agent, or Firm*—Schiff Hardin LLP

(57) ABSTRACT

A method and apparatus are used for training adjustment in sports, particularly in running sports, in which light is radiated into the body tissue of a test person by at least one light source, the light intensity reflected in the body tissue is measured via at least one light sensor, a temporally oscillating measurement quantity is derived from the measured light intensity via an evaluator, a minima in the time curve of the measurement quantity are determined, and a performance rating from which the current metabolic state of the test person can be read out is generated via analysis of a plurality of temporally successive minima and displayed.

14 Claims, 4 Drawing Sheets

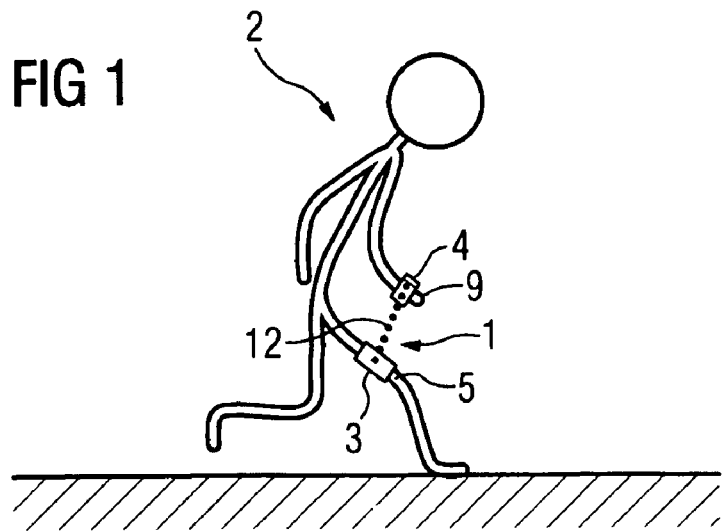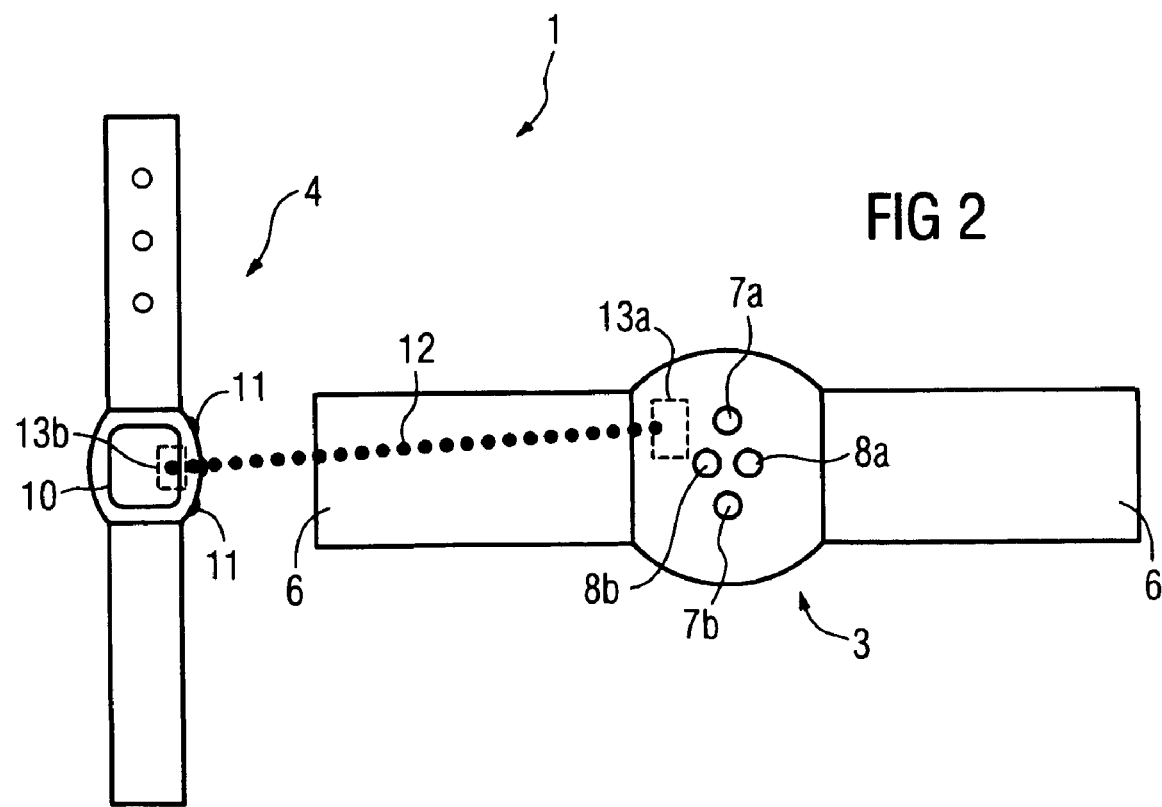

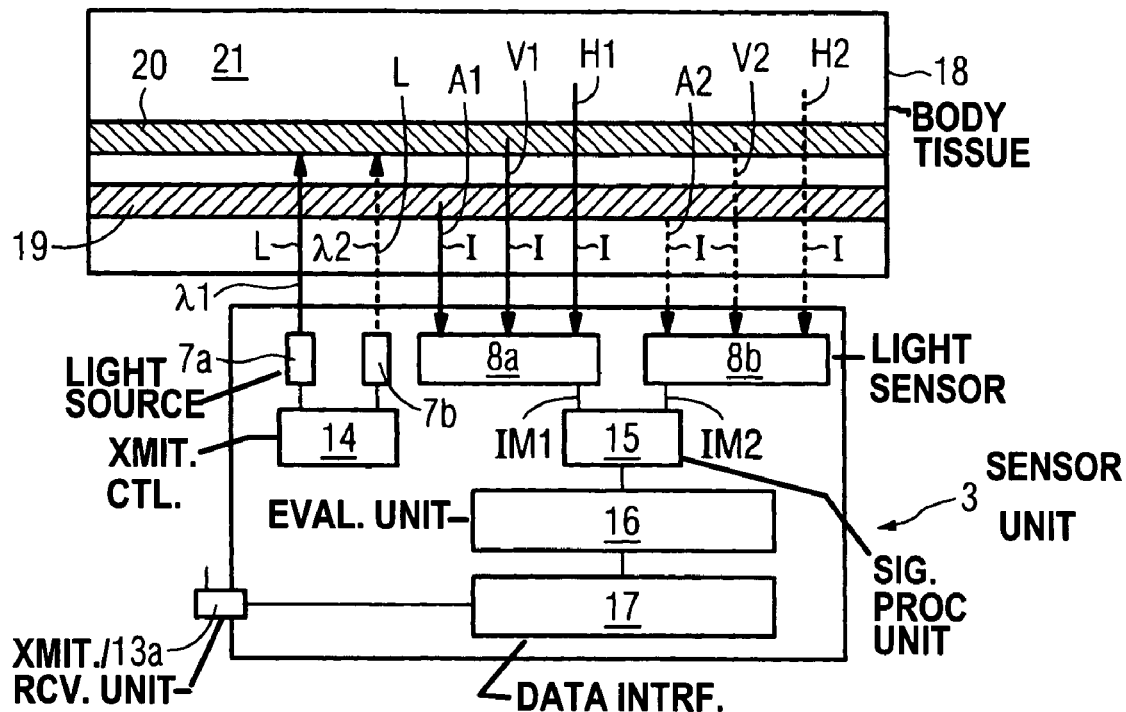
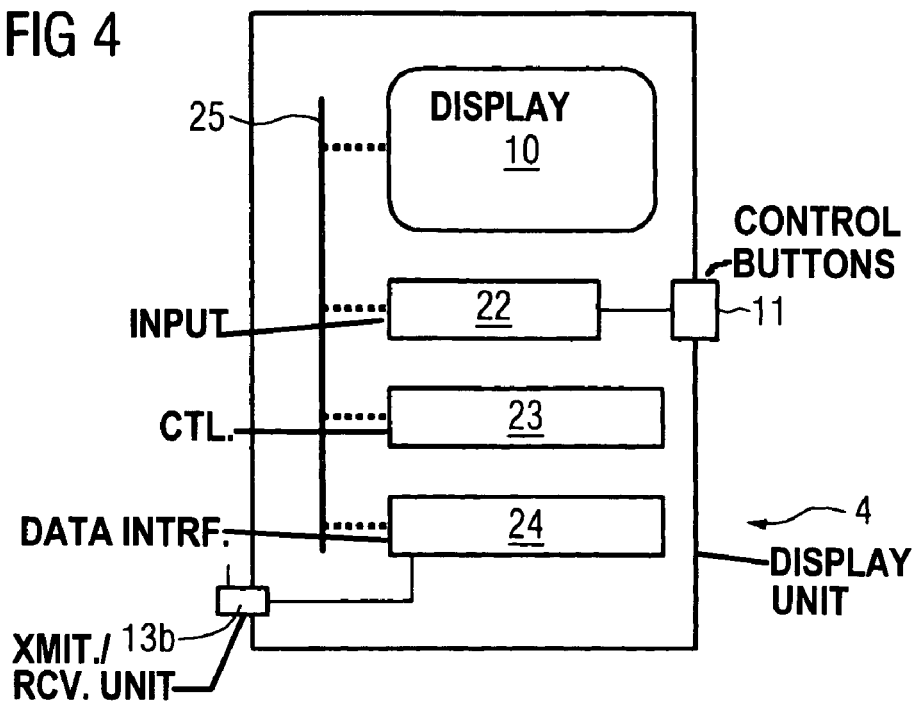

METHOD AND APPARATUS FOR TRAINING ADJUSTMENT IN SPORTS, IN PARTICULAR IN RUNNING SPORTS

BACKGROUND OF THE INVENTION

The invention concerns a method for training adjustment in sports, particularly running sports. The invention furthermore concerns an apparatus for execution of the method.

To generate muscle power, a muscle, specifically a human muscle, requires oxygen that must be supplied by the organism. The greater the power, the greater the need for oxygen. At a certain power limit, the body will go into what is known as "oxygen debt". This means that the blood contains too small of an oxygen ratio to be able to supply the oxygen necessary to generate power. The metabolism in the muscle then passes into the anaerobic range marked by oxygen deficiency. In contrast to this, the metabolism given sufficient oxygen supply is designated as aerobic.

Complete burning of the energy carrier glucose drawn on by the body does not ensue in the muscle in the anaerobic range. As a result of this, "combustion shortfalls" accumulate in the body that can no longer completely metabolized as a result of the oxygen deficiency. The muscle thus stressed becomes "acidic" and requires a longer time in order to regenerate after the stress.

In sport types that are connected with high body stress, particularly running sports, it is therefore important that the training is implemented predominantly in the aerobic range, and only a small portion in the anaerobic range. In an amateur athlete, for example, the aerobic training phase should amount to approximately 80% of the overall training.

For training adjustment, it is typical in sports medicine to determine the "lactate balance point" (LBP). Lactate (lactic acid) is a metabolic product of glucose that—as specified previously—is created when the oxygen in the organism is no longer sufficient for combustion. In the anaerobic range, lactate therefore accumulates in the body, while in the aerobic range excess lactate is metabolized again.

At the threshold between aerobic metabolism and anaerobic metabolism, the lactate level in the organism remains in balance. This defines the LBP. In reverse, the LBP is subsequently used as a synonym for the performance threshold at which the metabolism of the test subject passes from the aerobic range into the anaerobic range. The LBP is approximately characterized by associated measurement quantities of the organism, for example, an associated heart rate. If the heart rate of an athlete corresponding to the LBP is known, the athlete can optimize his training accordingly.

In running sports, a wearable pulse sensor is frequently used that determines the heart rate by way of a pulse band worn on the upper body of the athlete. However, using this pulse sensor, only a comparably rough training adjustment is possible. Using only the heart rate, only an imprecise estimate can be made as to whether the athlete temporarily undershoots or overshoots the LBP, and thus whether the athlete is temporarily located in the aerobic or anaerobic range.

The LBP can be determined via direct measurement of the lactate value. The lactate value is conventionally determined with a lactate measurement device which effects an analysis of blood that is extracted from the athlete at different degrees of stress. Physiological fundamentals and a method for lactate measurement are, for example, specified in German Patent Document No. DE 199 09 852 A1. The known solution is, disadvantageously, an invasive method, especially as blood samples must be extracted from the athlete to be tested (hereinafter, "test person"). This is, on the one hand, sometimes painful for the athlete. On the other hand, the blood extraction is always connected with a risk of infection, for example, with hepatitis or HIV, for both the test person and for the examiner. To reduce this infection risk, high hygiene standards are in turn necessary that make the method elaborate and expensive.

SUMMARY OF THE INVENTION

The invention is based on the object to provide an apparatus for training adjustment in sports, particularly running sports, with which a simple, precise and automatic performance determination of a test person is possible. Specifically, a non-invasive determination of the lactate balance point (LBP) should hereby be possible.

This object is achieved by a method for training control in sports, comprising: radiating light into body tissue of a test person; measuring light intensity reflected in the body tissue of the test person; deriving a temporally oscillating measurement quantity from the measured light intensity, determining a minima in a time curve of the measurement quantity; analyzing a plurality of temporally successive minima; generating a performance rating from which a current metabolic state of the test person can be read out via the analysis of the plurality of temporally successive minima; and displaying the generated performance rating.

This object is further achieved by an apparatus for training control in sports, comprising: at least one light source configured to radiate light into body tissue of a test person; at least one light sensor configured to measure light intensity reflected in the body tissue; and an evaluator configured to derive a temporally oscillating measurement quantity from the measured light intensity, to determine minima in a time curve of the measurement quantity, and to create a performance rating of the test person via analysis of a plurality of temporally successive minima, from which a current metabolic state of the test person can be read out.

The below described embodiments of the invention illustrate various inventive aspects. Light is radiated into the body tissue of a test person with a light source, and the light intensity reflected in the body tissue is measured with a light sensor. A temporally oscillating measurement quantity that is subsequently evaluated is derived from the measured light intensity with an evaluator.

The evaluator is fashioned to detect the periodically occurring minima in the time curve of the measurement quantity. Via analysis of a plurality of temporally successive minima, based on this, a subsequent characteristic quantity (designated as a performance quantity) is determined that enables information about the momentary metabolic state of the test person. This performance rating is shown to the test person.

The invention originates from the consideration that the lactate level in the blood only indirectly reproduces the current metabolic state of the test person. The metabolic state, and moreover in turn the LBP, would accordingly be more precisely determinable if it were achieved to be able to directly measure the oxygen content of the blood in the body tissue stressed by the exercise.

Embodiments of the invention utilize the common knowledge that a non-invasive measurement of the oxygen content in the blood is possible via radiation of light and analysis of the light reflected in the body tissue. Such a method as it is, for example, known from German Patent Document No. DE 696 04 464 T2 (German translation of European Patent Document No. EP 0 761 159 B1) is, however, conventionally provided and suited for determining the oxygen saturation in the arterial blood. The oxygen saturation in the arterial blood is, however, not, on the one hand, suitable or only barely suitable for determination of the metabolic state in the stressed body tissue, even more so as the arteries guide freshly mixed blood and blood enriched with oxygen.

On the other hand, the oxygen saturation of the venous blood accordingly reproduces the oxygen consumption of the body tissue very precisely. The conventional methodology for optical blood oxygen measurement in the arterial blood is now, inventively, specifically addressed in a manner such that the determination of the oxygen saturation in the venous blood, or an approximately proportional quantity for this, is now also possible. This is, according to embodiments of the invention, achieved in that the reflected light intensity, or a measurement quantity derived therefrom, is specifically evaluated in the ranges of minimal reflection, whereby the influence of the arterial blood is particularly weak.

A significant advantage of embodiments of the inventive method and the associated apparatus is that the method can be executed automatically in a very simple manner via an apparatus that can be realized in a very compact manner. The test person can therefore implement the method in a self-test with the aid of the apparatus. In particular, no trained personnel is thus necessary to implement the method, and therewith for the training adjustment of the test person. Furthermore, as a consequence of the compact size, the test person can carry the apparatus in a simple manner without the apparatus hindering the test person while performing.

The evaluation unit preferably recognizes the trend of temporally successive minima of the measurement quantity, whether the metabolism in the examined body tissue is aerobic or anaerobic, and outputs a performance rating corresponding with the finding. If the minimal value of the measurement quantity remains constant within predetermined boundaries, the evaluation unit recognizes the existence of an aerobic metabolic state. Otherwise the metabolism of the test person is detected as anaerobic.

From the period of the oscillating measurement quantity, the current heart rate of the test person is advantageously, additionally determined in order to provide the test person with a further observation quantity for the training adjustment.

In an embodiment of the invention, the LBP is determined in a simple manner via supervision of the performance rating during the training curve.

To display the current performance rating, a representation is appropriately selected from which the test person can recognize his current metabolic state in a particularly simple manner in order to ensure a high ease of use that does not demand an over-taxation of the test person, even given the highest personal exertion.

In this context, in particular a graphical representation of the performance rating, for example, via a bar graph, is particularly advantageous. Furthermore, what is also advantageous is the indirect representation of the performance rating using the current heart rate in comparison with the limit value of the heart rate (which corresponds with the LBP); typically in practice is the training adjustment using the heart rate. Instead of the heart rate, other quantities characteristic for the state of the organism can also be drawn upon, for example the oxygen saturation in the venous blood. The performance rating can furthermore also be represented in generic scales. For better representation of the performance rating, in particular color and sound signals can also be used. Various representation types of the performance rating are appropriately simultaneously shown to the test person. Furthermore, the test person can select between various display options.

The light radiation as well as the measurement of the reflected light intensity are advantageously effected at a predominantly stressed body part of the test person. This allows for the fact that, in most sport types, various parts of the musculature are stressed differently. Thus, for example, in running sports, leg muscles are predominantly stressed, while arm muscles are only stressed less than average. Therefore, for use in running sports, the light radiation and light measurement are provided at the thigh of the test person.

For a precise determination of the oxygen saturation in the venous blood, light of two wavelengths is appropriately radiated into the body tissue and the reflected light intensity at each of the wavelengths is measured separately. With this, the ratio of the absorption cross-sections of oxygen-saturated blood is taken into account on the one hand and oxygen-poor blood on the other hand is different at different wavelengths. Via comparison of the wavelength-dependent light reflection, the proportion of oxygen-containing blood and the reflection proportion of oxygen-poor blood can be determined particularly well.

A first wavelength is advantageously radiated at which the oxygen-saturated blood exhibits a particularly high absorption cross-section, while the second wavelength is selected such that the light of this wavelength is absorbed particularly well by oxygen-poor blood. In order to selectively measure reflected light at each wavelength, two light sensors are optionally provided, of which each selectively detects light of the one or the other wavelength.

Alternatively, the measurement of the reflected light intensity is provided for both wavelengths via a common light sensor. In order to enable a simple division of the reflection portions of the respective light wavelength, it is provided that the light of both wavelengths is alternately (meaning via alternating light pulses) radiated such that the respectively reflected light intensity of both light wavelengths is detected at different time intervals delimited from one another.

Only a part of the light reflected in the body tissue is reflected on the blood contained in the body tissue. This portion is overlaid by a further light portion that is reflected by the skin, the connective tissue, or the bones of the test person. This last light portion is nearly independent of the physical stress of the test person and is subsequently designated as a background reflection. To eliminate this, for determination of the blood oxygen saturation, noise-level background reflection of the body tissue may be provided to acquire a rest value of the measured light intensity before stressing the test person. This rest value is stored and subsequently drawn upon to compensate the background reflection.

A particularly simple method to implement such a calibration of the measurement quantity using the rest value is to subtract the rest value from the light intensity measured in the training course. Each deviation of the measured light intensity or of the derived measurement quantity from the associated rest value corresponds with a change of the oxygen saturation in the blood, which is dependent on the athletic performance; the background reflection is especially primarily performance-independent.

In order, on the one hand, to be able to effect the measurement of the oxygen saturation at the predominantly stressed body part of the test person, and in order, on the other hand, to be able to display the analysis result to the test person, an apparatus is appropriately divided into a sensor unit which comprises at least the minimum of one light source and the minimum of one light sensor, as well as a display unit which comprises at least the output unit.

The sensor unit is thereby appropriately attachable at a predominantly stressed body part of the test person in order to there be able to effect the measurement. In contrast to this, the display unit is preferably attachable to a location that is easily accessible and ideally visible for the test person. Given use in running sports, the display unit is preferably attachable to the wrist like a type of wristwatch. In contrast to this, in cycling it is, for example, sensible to execute the display unit such that it can be attached to the bicycle handlebars.

For data transmission, the sensor unit and the display unit are appropriately connected with one another via a data transmission path that, for simplification of the handling of the apparatus, is appropriately executed as a wireless data transmission path. Conventional mechanisms of wireless data transmission, for example, infrared transmission or radio transmission, lend themselves to data transmission.

DESCRIPTION OF THE DRAWINGS

Exemplary embodiments of the invention are subsequently explained in detail using the below-described drawing figures.

FIG. 1 is a pictorial schematic of a runner as a test person with an exemplary apparatus for training adjustment;

FIG. 2 is a schematic plan view of the apparatus according to FIG. 1, comprising a sensor unit and a display unit;

FIG. 3 is an exemplary schematic cross-sectional view of the sensor unit according to FIG. 2;

FIG. 4 is a block diagram representation of the display unit according to FIG. 2;

Parts and quantities corresponding with one another are provided with the same reference characters in the Figures.

DETAILED DESCRIPTION OF THE PREFERRED EMBODIMENTS

Figure 6:
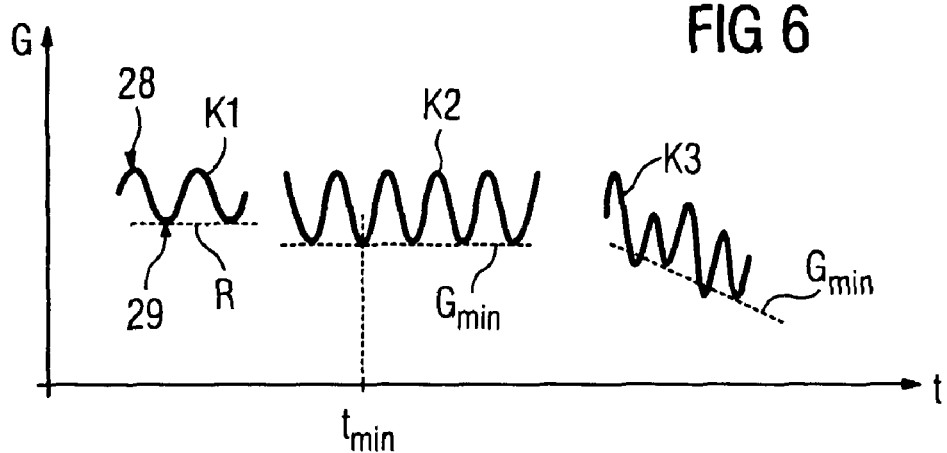
FIG. 6 is a graph showing an exemplary curve of a measurement quantity (drawn upon by the apparatus according to FIG. 2) in the rest state of the test person, in the aerobic training range and in the anaerobic training range.

In a schematic pictorial diagram, FIG. 1 shows the use of an apparatus for training adjustment of a test person 2 in sports. The shown exemplary embodiment of the apparatus 1 is particularly conceptualized for use in running sports. However, the apparatus 1 can also be used in the same manner for training adjustment in other sport types, for example, in cycling sports.

The apparatus 1, shown again in FIG. 2 in a schematic plan view, comprises a sensor unit 3 as well as a display unit 4. The sensor unit 3 serves for the measurement of the venous oxygen saturation in a body part of the test person 2 predominantly stressed in the sport. In running sports, the leg musculature is particularly predominantly stressed. The measurement of the venous oxygen saturation is therefore effected at the thigh 5 of the test person 2 as the predominantly stressed body part.

For this, the sensor unit may be executed as a band that can be attached to the thigh 5. The ends 6 of the band-like sensor unit 3 can, for example, be connected with a Velcro® fastener (not shown in detail). To measure the venous oxygen saturation, the sensor unit 3 comprises two light sources 7a and 7b to radiate light into the thigh 5 of the test person 2. The light sources 7a,7b are preferably realized via light-emitting diodes (LEDs). Due to their high light yield, low head development and very compact size, LEDs are particularly suited for this purpose. The sensor unit 3 furthermore comprises two light sensors 8a, 8b to measure the reflected light.

The display unit 4 is fashioned as a type of wristwatch and can be fastened to the wrist 9 of the test person. It comprises a display 10 as well as laterally attached control buttons 11 for selection of display options, parameterization of the apparatus 1, etc. The design (similar to a wristwatch) of the display unit 4 and its conventional attachment to the wrist is particularly advantageous in running sports, especially as the display 10 and the control buttons 11 can also be easily viewed or operated in this manner during the athletic exertion. Via the attachment of the apparatus 1 to the wrist 9 or thigh 5, it is simultaneously ensured that the apparatus 1 does not hinder the test person 2 in the athletic exertion.

For other sport types, a differentiated design of the display unit 4 can be advantageous. Thus the display unit for use in cycling is, for example, particularly advantageously to be realized as a component of a bicycle computer.

For communication purposes, the sensor unit 3 and the display unit 4 are connected with one another via a data transmission path 12. The data transmission path 12 is preferably executed wirelessly. As a part of the data transmission path 12, both the sensor unit 3 and the display unit 4 are therefore respectively provided with a transmission and reception unit 13a or 13b. The transmission and reception units 13a, 13b communicate via a conventional wireless data transmission technology, for example, infrared technology or radio technology.

The design of the sensor unit 3 is shown in detail in a schematic principle representation in FIG. 3. From this, it can be recognized that the light sources 7a and 7b are controlled by a transmission control 14. The light sensors 8a, 8b are for their part connected with an evaluation unit 16 via a signal processing unit 15. This is in turn connected with a data interface 17 that controls the transmission and reception unit 13a.

The transmission control 14 controls the light sources 7a and 7b such that these radiate light L into the (schematically indicated) body tissue 18 of the thigh 5. The body tissue 18 is composed of arteries 19, veins 20, and a remainder (subsequently designated simply as base tissue 21) that, in a non-differentiated manner, comprises skin, connective tissue, bones, etc.

A part of the radiated light L is reflected in the body tissue 18. The reflected light intensity I is comprised of a light portion that is reflected by the blood flowing through the arteries 19 and which is subsequently designated as arterial reflection A1, A2. A further portion is reflected by the blood contained in the veins 20. This portion is subsequently designated as venous reflection V1, V2. Finally, a part of the radiated light L is also reflected by the base tissue 21. This portion is designated as background reflection H1, H2.

Both of the light sources 7a, 7b radiate light of different wavelengths. The light source 7a hereby radiates light of a first wavelength $\lambda 1$, which is particularly strongly absorbed in the oxygen-saturated blood. This is in particular the case in the near-infrared light range with a wavelength of $\lambda 1 \approx 940$ nm. The second light source 7b radiates light L of a wavelength $\lambda 2$ which is particularly strongly absorbed in the oxygen-poor blood. In particular wavelengths in the range of $\lambda 2 \approx 600$ nm are suited for this.

Corresponding to both of the radiated wavelengths $\lambda 1$ and $\lambda 2$, the reflected light intensity also divides into portion A1, V1 and H1 that correspond to the wavelength $\lambda 1$ and portions A2, V2 and H2 that correspond to the wavelength $\lambda 2$.

The reflected light intensity I is detected selectively with regard to wavelength by the light sensors 8a, 8b. This is technically, preferably realized such that the light sensor 8a selectively detects light of the wavelength λ1 while the light sensor 8b selectively detects light of the wavelength λ2. Alternatively, a wavelength-selective light intensity measurement is also possible with a single light sensor when the light sources 7a and 7b are controlled such that they alternately emit light pulses, such that the light portions A1, V1, H1 (associated with the wavelength λ1) on the one hand and the light portions A2, V2 H2 (associated with the wavelength λ2) on the other hand respectively impinge on the light sensor at different times.

The light sensors 8a, 8b respectively generate a measurement signal that is characteristic for the reflected total intensity A1+V1+H1 or A2+V2+H2 of the respective wavelength λ1 or λ2 and is subsequently designated as measured light intensities IM1 or IM2. The measured light intensities IM1 and IM2 are amplified in the signal processing unit 15 and transduced into digital data.

The time curve of the measured light intensities IM1 and IM2 is evaluated in the evaluation unit 16 in a manner subsequently described. The evaluation result is subsequently conveyed to the display unit 4 via the data interface 17 and the transmission and reception unit 13a.

The display unit 4 is shown in detail in FIG. 4 in a schematic principle representation. In addition to the display 10, it additionally comprises an input module 22 communicating with the control buttons 11, a control unit 23, and a data interface 24 controlling the transmission and reception unit 13b. The display 10, the input module 22, the control unit 23 and the data interface 24 are connected with one another via bus and signal lines 25 for data transfer.

The data supplied to the display unit 4 by the sensor unit 3 are further processed in the control unit 23 and prepared for display. The result is subsequently displayed on the display 10. The control unit 23, which is fashioned as a microcontroller equipped with corresponding software, takes over the further general control functions. These are parameterized via the input module 22 cooperating with the control buttons 11. For example, display options can be adjusted via the control buttons 11, and user-specific data can be input as a parameter for the evaluation method.

Figure 5:
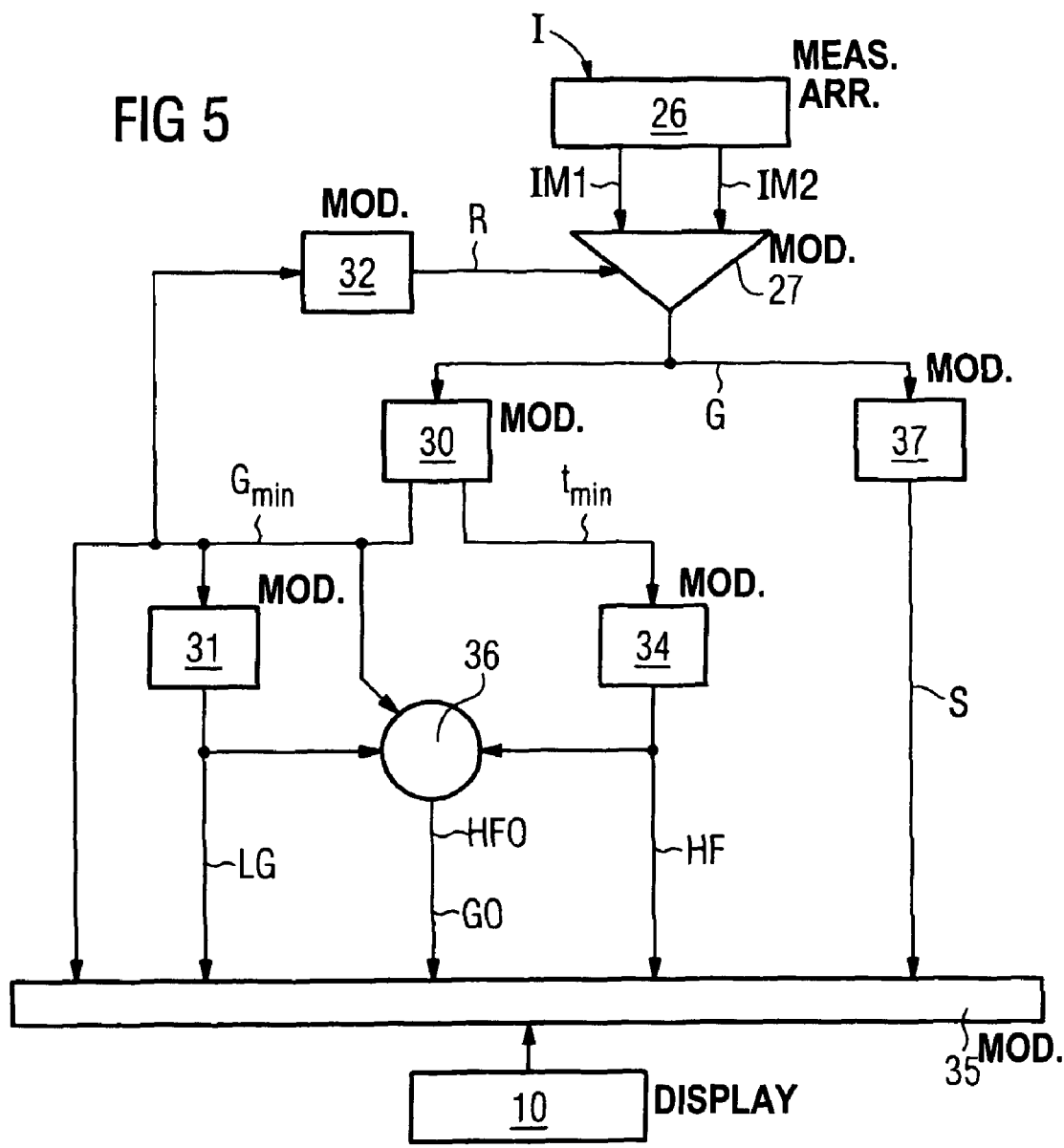
FIG. 5 in a simplified block diagram illustrating the method implemented by the apparatus according to FIG. 2.

The measurement and evaluation method executed in common by the evaluation unit 16 and the control unit 23 is shown in FIG. 5 in a schematic block diagram. The light intensity I reflected in the body tissue 18 and measured selectively with regard to wavelength is accordingly first measured by a measurement arrangement 26 that comprises the light sensors 8a and 8b as well as the signal processing device 15. The measured light intensity IM1 and IM2 are hereby generated as output data.

In a first module 27, a measurement quantity G (on which the further evaluation of the measurement results ensues) is derived via mathematical combination of the measured light intensities IM1 and IM2. The measured light intensities IM1 and IM2 are preferably combined such that the measurement quantity G represents a measure for the oxygen saturation in the blood of the body tissue 18. Such a calculation of the oxygen saturation of blood is known and is, for example, specified in B. Schöller, MCC GmbH (publisher) "Pulsoximetrie-Fibel, Theorie zur Pulsoximetrie, Kalibrierung und Messstabilität von Pulsoximetern", MCC GmbH, 2000, 2nd edition, chapter 3.

However, in principle other mathematical combinations of the measured light intensities IM1 and IM2 are also conceivable that likewise generate a measurement quantity G suitable for the subsequently specified evaluation. In particular, especially if the knowledge of the absolute value of the oxygen saturation in the blood is not absolutely necessary for the subsequently specified evaluation, the measurement quantity G could also be generated via averaging between the measured light intensities IM1 and IM2 or the like. In a still-simpler variant, it would also be conceivable to use the unmodified light intensities IM1 or IM2 as the measurement quantity G.

A characteristic of the light intensity I reflected in the body tissue 18 that is important for the subsequently specified evaluation is that the light intensity I temporally oscillates with the frequency of the heartbeat HF of the test person 2. This is primarily due to the blood flowing like pulses through the arteries 19 of the body tissue 18 at each heartbeat. The light portion A1, A2 reflected by the arteries 19 is therefore subject to a strong temporal fluctuation whose frequency corresponds to the heart rate HF. In contrast to this, the influence of the heartbeat on the blood flow in the veins 20 is significantly less pronounced, such that the venous reflection V1, V2 is only weakly temporally variable. The background reflection H1, H2 caused by the base tissue 21 is if anything time-independent as a good approximation.

The measurement quantity G reproduces the time dependence of the measured light intensities IM1, IM2 and correspondingly likewise oscillates with the heart rate HF. This is shown in the curve of the time t using curves K1, K2, K3 of the measurement quantity G shown schematically simplified in FIG. 6. The curve K1 thereby represents the curve of the measurement quantity G in the rest state of the test person 2, the curve K2, represents the curve of the measurement quantity G given aerobic stress, and the curve K3 represents the curve of the measurement quantity G given anaerobic stress.

Especially if the oscillation of the measurement quantity H is significantly based on the time dependence of the arterial reflection A1, A2, its influence is particularly strong in each maximum 28, thus each wave peak of the oscillating measurement quantity G, while the influence of the venous reflection V1, V2 on the measurement quantity G dominates in each minimum 29, thus each wave trough. It is therefore possible to specifically determine the venous oxygen saturation when the measurement quantity H is only evaluated in the range of the minima 29. For this purpose, the measurement quantity G is supplied to a module 30 (FIG. 5) which detects minima 29 in the time curve of the measurement quantity G via prevalent mathematical methods and determines their point in time tmin as well as the minimal value Gmin.

A further module 31 analyzes the temporal development of the minimal value Gmin for temporally successive minima 29 and, dependent on this temporal development, generates a characteristic quantity (subsequently designated as a performance rating L) that is characteristic for the current metabolic state of the test person 2. If the minimal value Gmin remains constant within predetermined tolerance values during a predetermined time interval, as this is shown using the curves K1 and K2 (FIG. 6), the module 31 outputs a performance rating L that indicates an aerobic metabolic state of the test person 2. In contrast to this, if the minimal value Gmin (as shown in the curve K3 of FIG. 6) is temporally not constant, the module 31 outputs a performance rating L that corresponds to an anaerobic metabolic state of the test person. The performance rating L is alternatively executed as a binary (for example, 0=aerobic, 1=anaerobic) quantity, a discretely differentiated (for example, . . . , −2, −1, 0=LBP, 1, 2, . . . ) quantity, or a continuously differentiated quantity.

Especially if the measurement quantity G oscillates with the frequency of the heartbeat, the heart rate HF can be determined in a simple manner from the temporal separation of the time points tmin of two successive minima 29. A further module 34 is provided for this. The performance rating L and the heart rate HF are supplied to a module 35 that prepares these data for display on the display 10. The test person 2 can thus call up his current heart rate HF and his current performance rating L at any time in the training course.

If, during the training course, the test person 2 exceeds the threshold (characterized by the LBP) between the aerobic metabolic range and the anaerobic metabolic range, the performance rating L also changes from a value that characterizes the aerobic state to a value that characterizes the anaerobic state. A module 26 monitors the value of the performance rating L during the training course, to the effect that the change between the anaerobic metabolic state and the anaerobic metabolic state of the test person is detected. When the metabolic state of the test person 2 corresponds to the LBP, the module 36 calls up the associated minimal value Gmin as well as the associated heart rate HF. These values, which correspond to the limit values G0 or, respectively, HF0 of the minimal value Gmin (and thus to the venous oxygen saturation) or the heart rate HF characteristic for the LBP, are supplied to the module 35 and stored as comparison values.

Optionally, a module 37 is additionally provided that filters out the maxima 28 from the time curve of the measurement quantity G and, in a known manner, determines the oxygen saturation S of the arterial blood.

Thus, in addition to the current values of the performance rating L and the heart rate HF, the limit values G0 and HF0 characteristic for the LBP are supplied to the module 35. The module 35 optionally also obtains the current value of the arterial oxygen saturation S. These values can be displayed on the display 10 by the module 35 individually or combined in a manner selectable by the test person 2.

Furthermore, a module 32 is optionally provided that, before the beginning of training, meaning in the rest state of the test person 2, retrieves the minimal value Gmin (FIG. 6, curve K1) and stores it as a rest value R. This rest value R can be subtracted from the current value of the measurement quantity G in the course of training for calibration of the apparatus 1. The influence of the stress-independent background reflection H1, H2 is hereby particularly eliminated.

Figure 7:
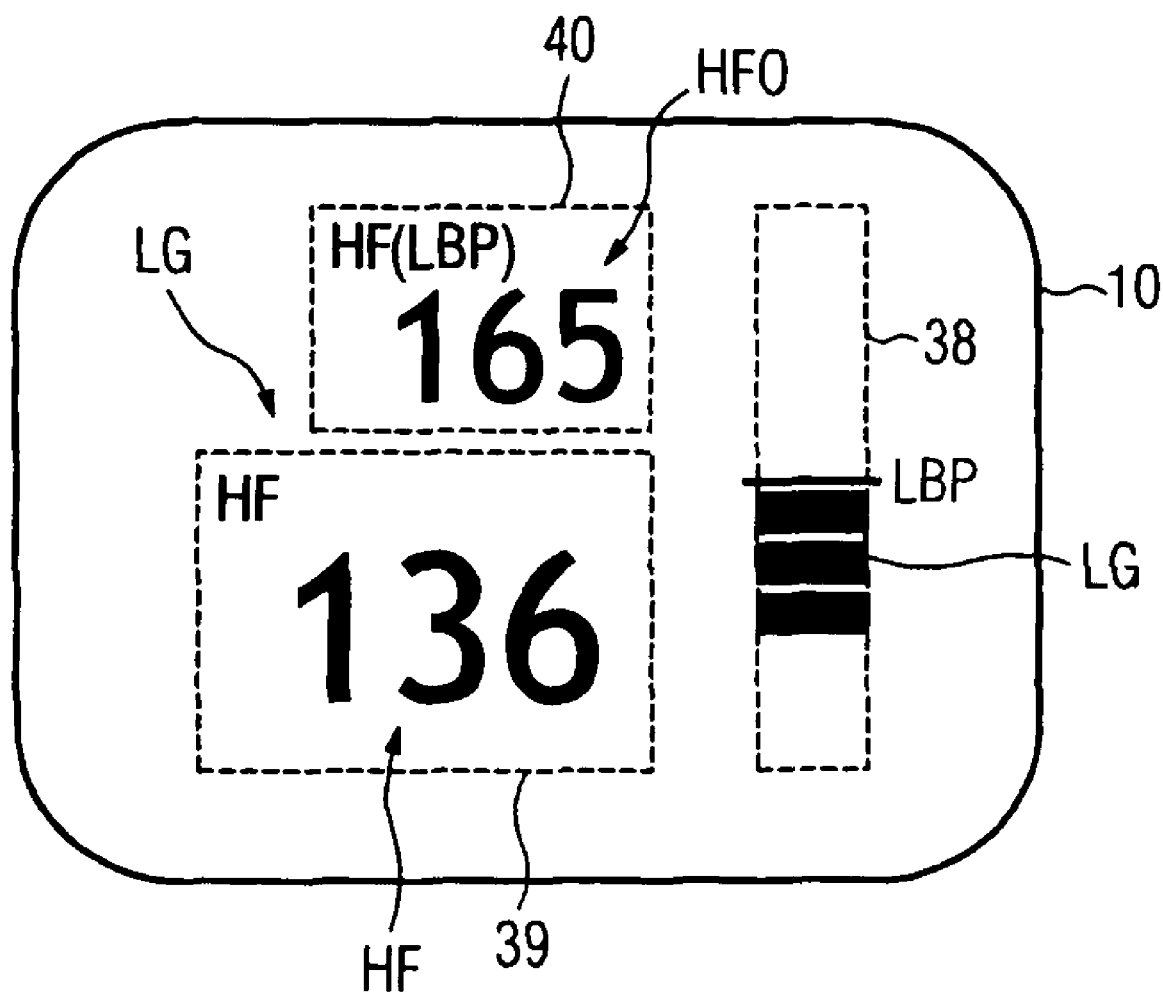
FIG. 7 is a pictorial diagram for an exemplary display of the performance rating determined by the apparatus according to FIG. 2 and displayed to the test person.

In an exemplary view of the display 10, FIG. 7 shows two variants to show the current performance rating L in an easily recognizable manner for the test person 2. The performance rating L is shown on the one hand in the form of a bar diagram 38. The LBP may be characterized by the zero line of the bar diagram 38. A negative amplitude of the bar diagram 38, as it is exemplarily shown in FIG. 7, indicates to the test person 2 that his metabolic state is aerobic. In contrast to this, positive amplitudes of the bar diagram 38 would indicate an anaerobic metabolic state. The test person 2 can moreover recognize from the bar height of the bar diagram 38 how far his current metabolic state is removed from the LBP.

In contrast to this, the left region of the display 10 contains two number fields 39 and 40. The first number field 39 serves for the display of the current heart rate HF of the test person 2. In contrast to this, the second number field serves for the display of the limit value HF0 of the heart rate, which corresponds to the LBP. Via the comparison of both of these numbers, the test person 2 can in turn recognize in which metabolic state he is currently located. If the current heart rate HF is lower than the limit value HF0, an aerobic metabolic state exists. In contrast to this, if the current heart rate HF exceeds the limit value HF0, the metabolic state of the rest person 2 is anaerobic.

Instead of the heart rate, the venous oxygen saturation could also be shown in the number fields 39 and 40. To mark the performance rating L, color and/or sound signals can also be resorted to for support. It is furthermore conceivable to display a temporal signal integrated over the performance rating L on the screen 10. In this case, the test person 2 could recognize not only in which metabolic range he is currently staying, but rather he could additionally obtain information about how long he has stayed in one of the two metabolic ranges, as well as possibly whether the temporal behavior of both of the metabolic ranges have been balanced or unbalanced in the prior training course.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

| REFERENCE LIST | |
| --- | --- |
| 1 | apparatus |
| 2 | test person |
| 3 | sensor unit |
| 4 | display unit |
| 5 | thigh |
| 6 | end |
| 7a, 7b | light source |
| 8a, 8b | light sensor |

-continued

REFERENCE LIST

| | |
|---|---|
| 9 | wrist |
| 10 | display |
| 11 | control buttons |
| 12 | data transmission path |
| 13a, 13b | transmission and reception unit |
| 14 | transmission control |
| 15 | signal processing unit |
| 16 | evaluation unit |
| 17 | data interface |
| 18 | body tissue |
| 19 | arteries |
| 20 | veins |
| 21 | base tissue |
| 22 | input module |
| 23 | control unit |
| 24 | data interface |
| 25 | bus and signal lines |
| 26 | measurement arrangement |
| 27 | module |
| 28 | maximum |
| 29 | minimum |
| 30 | module |
| 31 | module |
| 32 | module |
| 34 | module |
| 35 | module |
| 36 | module |
| 37 | module |
| 38 | bar diagram |
| 39 | number field |
| 40 | number field |
| LBP | lactate balance point |
| L | light |
| I | reflected light intensity |
| A1, A2 | arterial reflection |
| V1, V2 | venous reflection |
| H1, H2 | background reflection |
| $\lambda 1, \lambda 2$ | wavelength |
| IM1, IM2 | measured light intensity |
| G | measurement quantity |
| HF | heart rate |
| K1-K3 | curve |
| t | time |
| tmin | point in time (of the minimum) |
| Gmin | minimal value |
| L | performance rating |
| G0 | limit value (of the minimal value at the LBP) |
| HF0 | limit value (of the hear rate at the LBP) |
| S | oxygen saturation (of the arterial blood) |
| R | rest value |

What is claimed is:

1. A method for training control of a test person in sports, comprising the steps of:

radiating light into body tissue of the test person from outside the body of the test person into the body of the test person at a thigh of the test person which is highly stressed;

measuring light intensity reflected in venous blood in the body tissue of the thigh of the test person;

using an evaluator with an evaluation circuit, deriving a temporally oscillating measurement quantity from the measured light intensity which temporally oscillates corresponding to a heart rate of the test person where each heart rate induced oscillation is substantially the same as the previous oscillation at least during a rest state and an aerobic state of the test person;

determining a plurality of temporally successive minima in a time curve of the measurement quantity at a bottom of each said heart rate induced oscillation;

defining the rest state of the test person when said plurality of temporally successive minima remain substantially constant at a first value, determining the aerobic state for the test person when said plurality of temporally successive minima remain substantially constant at a second value which is less than said first value, and determining an anaerobic state for said test person when said temporally successive minima are not constant but are falling with time so that decreasing values result which are below said second value;

analyzing said plurality of temporally successive minima;

generating via the analysis of the plurality of temporally successive minima a quantity characterizing oxygen saturation in the venous blood as a performance rating from which a current metabolic state of the test person can be read out; and displaying the generated performance rating.

2. The method according to claim 1, further comprising:
determining a current heart rate of the test person from a period of the oscillating measurement quantity.

3. The method according to claim 1, further comprising:
determining a lactate balance point of the test person using the performance rating.

4. The method according to claim 1, further comprising:
displaying the performance rating in a graphic representation.

5. The method according to claim 1, further comprising:
determining, to represent the performance rating, a current heart rate of the test person in relation with a limit value to decide if the current heart rate corresponds to a lactate balance point.

6. The method according to claim 1, further comprising:
utilizing the light radiation and the measurement of the reflected light intensity on a predominantly stressed body part of the test person.

7. The method according to claim 1, further comprising:
radiating light of at least two wavelengths; and
measuring the reflected light intensity selectively with regard to wavelength.

8. The method according to claim 1, further comprising:
acquiring a rest value of the measured light intensity or of the measurement quantity before exertion of the test person; and
utilizing the rest value to compensate reflected background reflection of the body tissue.

9. The method according to claim 8, further comprising:
subtracting the rest value from the measured light intensity or the measurement quantity.

10. An apparatus for training control of a test person in sports, comprising:

at least one light source configured to radiate light into body tissue of the test person from outside the body of the test person into the body of the test person at a thigh of the test person which is highly stressed;

at least one light sensor configured to measure light intensity reflected in venous blood in the body tissue of the thigh;

an evaluator configured to derive a temporally oscillating measurement quantity from the measured light intensity which temporally oscillates corresponding to a heart rate of the test person where each heart rate induced oscillation is substantially the same as the previous oscillation at least having a rest state and an aerobic state of the test person, to determine a plurality of temporally successive minima in a time curve of the measurement quantity at a bottom of each said heart rate induced oscillation, and via an analysis of the plurality of temporally successive minima, determining a quantity characterizing oxygen saturation in the venous blood as a performance rating of the test person from which a current metabolic state of the test person can be read out; and said evaluator comprising an evaluation circuit which defines the rest state of the test person when said plurality of temporally successive minima remain substantially constant at a first value, determines the aerobic state for the test person when said plurality of temporally successive minima remain substantially constant at a second value which is less than said first value, and determines an anaerobic state for said test person when said temporally successive minima are not constant but are falling with time so that decreasing values result which are below said second value.

11. The apparatus according to claim 10, wherein the evaluator is configured to determine a current heart rate of the test person from a period of the oscillating measurement quantity.

12. The apparatus according to claim 10, wherein the at least one light source comprises:

a first light source configured to radiate light of a first wavelength into the body tissue; and a second light source configured to radiate light of a second wavelength into the body tissue;

wherein the at least one light sensor is configured to selectively measure the reflected light intensity with regard to the light wavelength.

13. The apparatus according to claim 10, further comprising:

a sensor unit which comprises the at least one light source and that comprises the at least one light sensor, the sensor unit configured to be attached to a predominantly stressed body part of the test person;

a display unit which comprises an output unit, configured to be attached to a location easily accessible to the test person; and a communications interface configured to connect the sensor unit and the display unit via a data transmission path.

14. The apparatus according to claim 13, wherein the data transmission path is a wireless data transmission path.

* * * * *